(12) United States Patent
Rotondo et al.

(10) Patent No.: US 7,319,736 B2
(45) Date of Patent: *Jan. 15, 2008

(54) REAL-TIME DIGITAL X-RAY IMAGING APPARATUS

(75) Inventors: Giuseppe Rotondo, Milan (IT); Gianfranco Venturino, Milan (IT)

(73) Assignee: Gendex Corporation, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/345,465

(22) Filed: Feb. 1, 2006

(65) Prior Publication Data

US 2006/0126780 A1 Jun. 15, 2006

Related U.S. Application Data

(63) Continuation of application No. 10/205,257, filed on Jul. 25, 2002, now Pat. No. 7,016,461.

(51) Int. Cl.
*A61B 6/14* (2006.01)

(52) U.S. Cl. .......................... 378/39; 378/197
(58) Field of Classification Search ............ 378/38–40, 378/168, 177, 191, 195–198
See application file for complete search history.

(56) References Cited

U.S. PATENT DOCUMENTS 3,894,235 A 7/1975 Franke
3,911,273 A 10/1975 Franke (Continued)

FOREIGN PATENT DOCUMENTS

CA 1259711 9/1989

(Continued)

OTHER PUBLICATIONS

D.B. Forsyth et al. "Digital Imaging of Cephalometric Radiography, Part 1: Advantages and Limitations of Digital Imaging"; The Angle Orthodontist, vol. 66, No. 1, 1996; pp. 37-42.

(Continued)

*Primary Examiner*—Hoon Song
(74) *Attorney, Agent, or Firm*—McNees Wallace & Nurick LLC

(57) ABSTRACT

An x-ray diagnostic apparatus and methods performs Real-Time Digital Radiography with particular application in dental x-ray imaging modalities, such as Orthopantomography, Scannography, Linear Tomography and Cephalography, by using a versatile and modular electronic unit, featuring ultra fast computation capability to serve diversified image sensor typology and scanning modality. In Digital Orthopantomography and Scannography, a plurality of tomographic images at different depths of the jaw can be generated, based on the pre-selection made by the user interface. The image processing unit utilizes for the tomosynthesis of the diagnostic image an accurate and economic digital simulator of the radiographic film speed, including a digital frequency synthesizer fed with film cassette speed digital input and high resolution clock signal, ensuring accurate and reproducible phase continuity of the output frequency signal. It also introduces an automatic adaptation of the frame acquisition rate in frame transfer mode, based on the actual speed of the cassette unit. By this method the dynamic of the exposure signal is reduced, and a better optimization of the signal response of the x-ray detector is achieved.

12 Claims, 3 Drawing Sheets

U.S. PATENT DOCUMENTS

| | | |
|---|---|---|
| 3,974,385 A | 8/1976 | Grim |
| 3,987,281 A | 10/1976 | Hodes |
| 3,991,314 A | 11/1976 | Schmitman et al. |
| 4,021,672 A | 5/1977 | Franke |
| 4,029,540 A | 6/1977 | Weidanz et al. |
| 4,061,920 A | 12/1977 | Mollendorf et al. |
| 4,070,578 A | 1/1978 | Timothy et al. |
| 4,097,741 A | 6/1978 | Pfeiler et al. |
| 4,104,531 A | 8/1978 | Weiss |
| 4,158,138 A | 6/1979 | Hellstrom |
| 4,160,906 A | 7/1979 | Daniels et al. |
| 4,160,997 A | 7/1979 | Schwartz |
| 4,188,537 A | 2/1980 | Franke |
| 4,241,254 A | 12/1980 | Valila |
| 4,247,780 A | 1/1981 | Webber et al. |
| 4,259,582 A | 3/1981 | Albert |
| 4,352,987 A | 10/1982 | Hayashi et al. |
| 4,361,764 A | 11/1982 | Zieler |
| 4,411,012 A | 10/1983 | Pfeiler et al. |
| 4,454,606 A | 6/1984 | Relihan |
| 4,475,224 A | 10/1984 | Grassme |
| 4,486,896 A | 12/1984 | Richter et al. |
| 4,495,632 A | 1/1985 | Nakano |
| 4,501,010 A | 2/1985 | Grassme |
| 4,521,899 A | 6/1985 | Finkenzeller |
| 4,589,121 A | 5/1986 | Makimo |
| 4,603,427 A | 7/1986 | Alpern et al. |
| 4,641,331 A | 2/1987 | Makino et al. |
| 4,661,967 A | 4/1987 | Nishikawa |
| 4,672,646 A * | 6/1987 | Van Maren ............ 377/70 |
| 4,675,888 A | 6/1987 | Gastrin |
| 4,683,581 A | 7/1987 | Tammisalo et al. |
| 4,683,582 A | 7/1987 | Spolyar |
| 4,741,007 A | 4/1988 | Virta et al. |
| 4,783,793 A | 11/1988 | Virta et al. |
| 4,797,905 A | 1/1989 | Ochmann |
| 4,811,372 A | 3/1989 | Doebert et al. |
| 4,813,060 A | 3/1989 | Heubeck et al. |
| 4,815,115 A | 3/1989 | Nieminen et al. |
| 4,823,369 A | 4/1989 | Guenther et al. |
| 4,847,881 A | 7/1989 | Heubeck |
| 4,856,038 A | 8/1989 | Guenther et al. |
| 4,878,234 A | 10/1989 | Pfeiffer et al. |
| 4,905,265 A | 2/1990 | Cox et al. |
| 4,930,146 A | 5/1990 | Flakas et al. |
| 4,980,905 A | 12/1990 | Meccariello |
| 4,985,907 A | 1/1991 | Moteni |
| 4,995,062 A | 2/1991 | Schulze-Ganzlin et al. |
| 4,995,107 A | 2/1991 | Klingenbeck |
| 5,005,195 A | 4/1991 | Lanza et al. |
| 5,012,501 A | 4/1991 | Palonen et al. |
| 5,018,177 A | 5/1991 | McDavid et al. |
| 5,033,070 A | 7/1991 | Kanerva et al. |
| 5,043,582 A | 8/1991 | Cox et al. |
| 5,058,147 A | 10/1991 | Nishikawa et al. |
| 5,077,769 A | 12/1991 | Franciose |
| 5,090,040 A | 2/1992 | Lanza et al. |
| 5,090,047 A | 2/1992 | Angotti et al. |
| 5,093,852 A | 3/1992 | Nishikawa et al. |
| 5,195,114 A | 3/1993 | Sairenji et al. |
| 5,212,737 A | 5/1993 | Ackelsberg |
| 5,214,686 A | 5/1993 | Webber |
| 5,267,296 A | 11/1993 | Albert |
| 5,293,312 A | 3/1994 | Waggener |
| 5,331,166 A | 7/1994 | Yamamoto et al. |
| 5,355,398 A | 10/1994 | Nakano et al. |
| 5,371,775 A | 12/1994 | Kanerva et al. |
| 5,386,448 A | 1/1995 | Tammisalo et al. |
| D355,964 S | 2/1995 | Nelvig |
| 5,425,065 A | 6/1995 | Jarvenin |
| 5,434,418 A | 7/1995 | Schick |
| 5,436,950 A | 7/1995 | Pauli et al. |
| 5,454,022 A | 9/1995 | Lee et al. |
| 5,454,023 A | 9/1995 | Asikainen |
| 5,469,429 A | 11/1995 | Yamazaki et al. |
| 5,473,660 A | 12/1995 | Bastiaens et al. |
| 5,483,091 A * | 1/1996 | West et al. ............ 257/239 |
| 5,490,197 A | 2/1996 | Albert et al. |
| 5,506,879 A | 4/1996 | Mori et al. |
| 5,511,106 A | 4/1996 | Doebert et al. |
| 5,513,252 A | 4/1996 | Blaschka et al. |
| 5,519,437 A | 5/1996 | Nelvig |
| 5,519,751 A | 5/1996 | Yamamoto et al. |
| 5,541,974 A | 7/1996 | Sklebitz |
| 5,579,361 A | 11/1996 | Augais et al. |
| 5,579,366 A | 11/1996 | Doebert et al. |
| 5,583,905 A | 12/1996 | Nishiki et al. |
| 5,590,164 A | 12/1996 | Kawai et al. |
| 5,590,167 A | 12/1996 | Yoshinori |
| 5,600,699 A | 2/1997 | Suzuki et al. |
| 5,602,896 A | 2/1997 | Diepstraten |
| 5,608,455 A | 3/1997 | Oda |
| 5,617,462 A | 4/1997 | Spratt |
| 5,625,662 A | 4/1997 | Toth et al. |
| 5,640,018 A | 6/1997 | Suzuki et al. |
| 5,663,998 A | 9/1997 | Suzuki et al. |
| 5,664,001 A | 9/1997 | Tachibana et al. |
| 5,666,392 A | 9/1997 | Ploetz et al. |
| 5,668,375 A | 9/1997 | Petrick et al. |
| 5,677,940 A | 10/1997 | Suzuki et al. |
| 5,692,027 A | 11/1997 | Yoshimura et al. |
| 5,694,448 A | 12/1997 | Morcom |
| 5,708,503 A | 1/1998 | Carrieri |
| 5,742,659 A | 4/1998 | Atac et al. |
| 5,744,806 A | 4/1998 | Frojd |
| 5,751,783 A | 5/1998 | Granfors et al. |
| 5,757,011 A | 5/1998 | Whitebook et al. |
| 5,773,832 A | 6/1998 | Sayed et al. |
| 5,784,429 A | 7/1998 | Arai |
| 5,793,837 A | 8/1998 | Mezhinsky et al. |
| 5,796,430 A | 8/1998 | Katoh et al. |
| 5,812,191 A | 9/1998 | Orava et al. |
| 5,828,720 A | 10/1998 | Syrjanen |
| 5,828,721 A | 10/1998 | Schulze-Ganzlin et al. |
| 5,848,123 A | 12/1998 | Strommer |
| 5,864,146 A | 1/1999 | Karellas |
| 5,878,104 A | 3/1999 | Ploetz |
| 5,887,049 A | 3/1999 | Fossum |
| 5,892,227 A | 4/1999 | Schieber et al. |
| 5,912,942 A | 6/1999 | Schick et al. |
| 5,921,927 A | 7/1999 | McArdle |
| 5,923,722 A | 7/1999 | Schulz |
| 5,930,330 A | 7/1999 | Wolfe et al. |
| 5,933,471 A | 8/1999 | Kalvin |
| 5,969,360 A | 10/1999 | Lee |
| 5,974,166 A | 10/1999 | Ino et al. |
| 5,997,176 A | 12/1999 | Fairleigh |
| 6,002,742 A | 12/1999 | Nelvig |
| 6,009,147 A | 12/1999 | Stein et al. |
| 6,035,013 A | 3/2000 | Orava et al. |
| 6,044,131 A | 3/2000 | McEvoy et al. |
| 6,047,042 A | 4/2000 | Khutoryansky et al. |
| 6,055,292 A | 4/2000 | Zeller et al. |
| 6,069,935 A | 5/2000 | Schick et al. |
| 6,081,739 A | 6/2000 | Lemchen |
| 6,093,019 A | 7/2000 | Morandi et al. |
| 6,094,467 A | 7/2000 | Gayer et al. |
| 6,118,842 A | 9/2000 | Arai et al. |
| 6,169,780 B1 * | 1/2001 | Yoshimura et al. ......... 378/39 |
| 6,173,035 B1 | 1/2001 | Tachibana et al. |
| 6,185,271 B1 | 2/2001 | Kinsinger |
| 6,205,199 B1 | 3/2001 | Polichal et al. |
| 6,208,706 B1 | 3/2001 | Campbell et al. |
| 6,243,439 B1 | 6/2001 | Arai et al. |

| | | |
|---|---|---|
| 6,289,074 B1 | 9/2001 | Arai et al. |
| 6,325,537 B1 | 12/2001 | Watanabe |
| 6,351,519 B1 | 2/2002 | Bonk et al. |
| 6,385,279 B1 | 5/2002 | Toth et al. |
| 6,452,997 B1 | 9/2002 | Muller et al. |
| 6,466,641 B1 | 10/2002 | Virta et al. |
| 6,470,069 B1 | 10/2002 | Muller |
| 6,570,953 B1 | 5/2003 | Dobert et al. |
| 6,584,171 B2 * | 6/2003 | Suzuki et al. .............. 378/98.8 |
| 6,731,717 B2 | 5/2004 | Kopsala |
| 6,798,453 B1 | 9/2004 | Kaifu |
| 6,829,326 B2 | 12/2004 | Woods |
| 6,891,921 B2 | 5/2005 | Kopsala |
| 7,016,461 B2 * | 3/2006 | Rotondo et al. .............. 378/39 |
| 7,092,483 B2 | 8/2006 | Nyholm |
| 7,103,141 B2 | 9/2006 | Sonobe et al. |

FOREIGN PATENT DOCUMENTS

| | | |
|---|---|---|
| DE | 42 38 268 | 5/1994 |
| DE | 44 33 545 | 3/1996 |
| DE | 196 48 076 | 5/1997 |
| DE | 196 48 052 | 6/1998 |
| DE | 197 54 463 | 6/1998 |
| DE | 197 31 927 | 2/1999 |
| DE | 197 34 717 | 2/1999 |
| EP | 0193650 | 10/1986 |
| EP | 0 229 497 | 7/1987 |
| EP | 0 234 603 | 9/1987 |
| EP | 0279294 | 8/1988 |
| EP | 0 373 717 | 6/1990 |
| EP | 0 408 167 | 1/1991 |
| EP | 0415075 | 3/1991 |
| EP | 0534 548 B1 | 3/1993 |
| EP | 0 574 368 | 12/1993 |
| EP | 0 632 994 | 1/1995 |
| EP | 0 632 995 | 1/1995 |
| EP | 0 634 671 | 1/1995 |
| EP | 0 673 623 | 9/1995 |
| EP | 1259162 B1 | 11/1995 |
| EP | 0 685 201 | 12/1995 |
| EP | 0 776 124 | 5/1997 |
| EP | 0 776 149 | 5/1997 |
| EP | 0 858 773 | 8/1998 |
| EP | 0973047 | 1/2000 |
| EP | 0724729 | 4/2000 |
| EP | 1013079 | 6/2006 |
| GB | 2304017 | 3/1997 |
| JP | 62 222 780 | 9/1987 |
| JP | 06000181 | 1/1994 |
| JP | 3 109 057 | 6/1998 |
| JP | 3261262 B2 | 2/2002 |
| WO | WO 89/07322 | 8/1989 |
| WO | WO 90/14793 | 12/1990 |
| WO | WO 91/15786 | 10/1991 |
| WO | 9222188 | 12/1992 |
| WO | WO 93/00046 | 1/1993 |
| WO | WO 93/00649 | 1/1993 |
| WO | WO 93/11707 | 6/1993 |
| WO | WO 93/14418 | 7/1993 |
| WO | WO 93/23952 | 11/1993 |
| WO | WO 94/12855 | 6/1994 |
| WO | WO 96/32064 | 10/1996 |
| WO | WO 98/56214 | 12/1998 |
| WO | 9908440 | 2/1999 |
| WO | WO 99/17659 | 4/1999 |
| WO | WO 99/62404 | 12/1999 |
| WO | WO 01/28298 | 4/2001 |
| WO | WO 01/66012 | 9/2001 |

OTHER PUBLICATIONS

R.M. Harrison, "Digital Radiography"; Phys. Med. Biol., 1988, vol. 33, No. 7, pp. 751-784; Printed in the UK; IOP Publishing Ltd.

M.J. Yaffe and J.A. Rowlands; "X-Ray Detectors for Digital Radiography"; Phys. Med. Biol. 42(1997), pp. 1-39; Printed in the UK; Imaging Research Program, Synnybrook Health Science Centre. The University of Toronto, Toronto, Ontario, Canada; PII: S0031-9155(97)36090-4; 1997 IOP Publishing Ltd.

Ann Wenzel and Hans-Goran Grondahl; "Direct Digital Radiography in the Dental Office"; International Dental Journal (1995) vol. 45, pp. 27-34; FDI/World Dental Press 1995.

William D. McDavid et al.; "Direct Digital Extraoral Radiography of the Head and Neck With a Solid-State Linear X-Ray Detector"; Dept. of Dental Diagnostic Science, University of Texas Health Science Center at San Antonio and Dept. of Oral Radiology, Karolinska Institute; Oral Surg. Oral Med Oral Pathol, Dec. 1992; vol. 74, No. 6, pp. 811-817.

A.R. Cowen et al.; "Direct Digital Mammography Image Acquisition"; Eur. Radiol. 7, pp. 918-930 (1997); Springer-Verlag 1997.

Y.J. Chen et al. "Comparison of Landmark Identification in Traditional Versus Computer-Aided Digital Cephalometry", The Angle Orthodontist, vol. 70, No. 5, pp. 384-392.

S. Dove et al. "Digital Panoramic and Extraoral Imaging", Dental Clinics of North America, Oct. 1998, vol. 37, No. 4, pp. 541-551.

D.B. Forsyth et al. "Digital Imaging of Cephalometric Radiography, Part 2: Image Quality", The Angle Orthodontist, vol. 66, No. 1, 1996; pp. 43-50.

H. Visser et al. "Dose Reduction by Direct-Digital Cephalometric Radiography"; The Angle Orthodontist, vol. 71, No. 3, pp. 159-163.

* cited by examiner

FIG_1: System outline
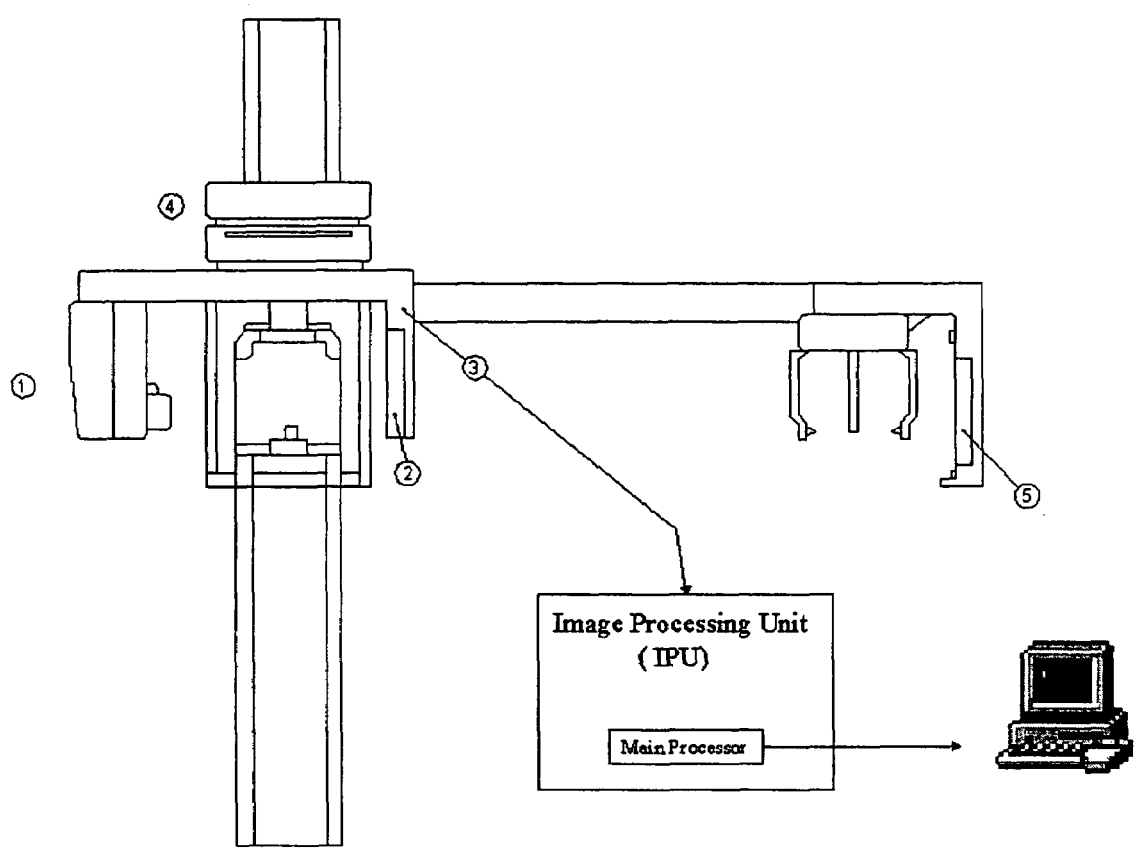

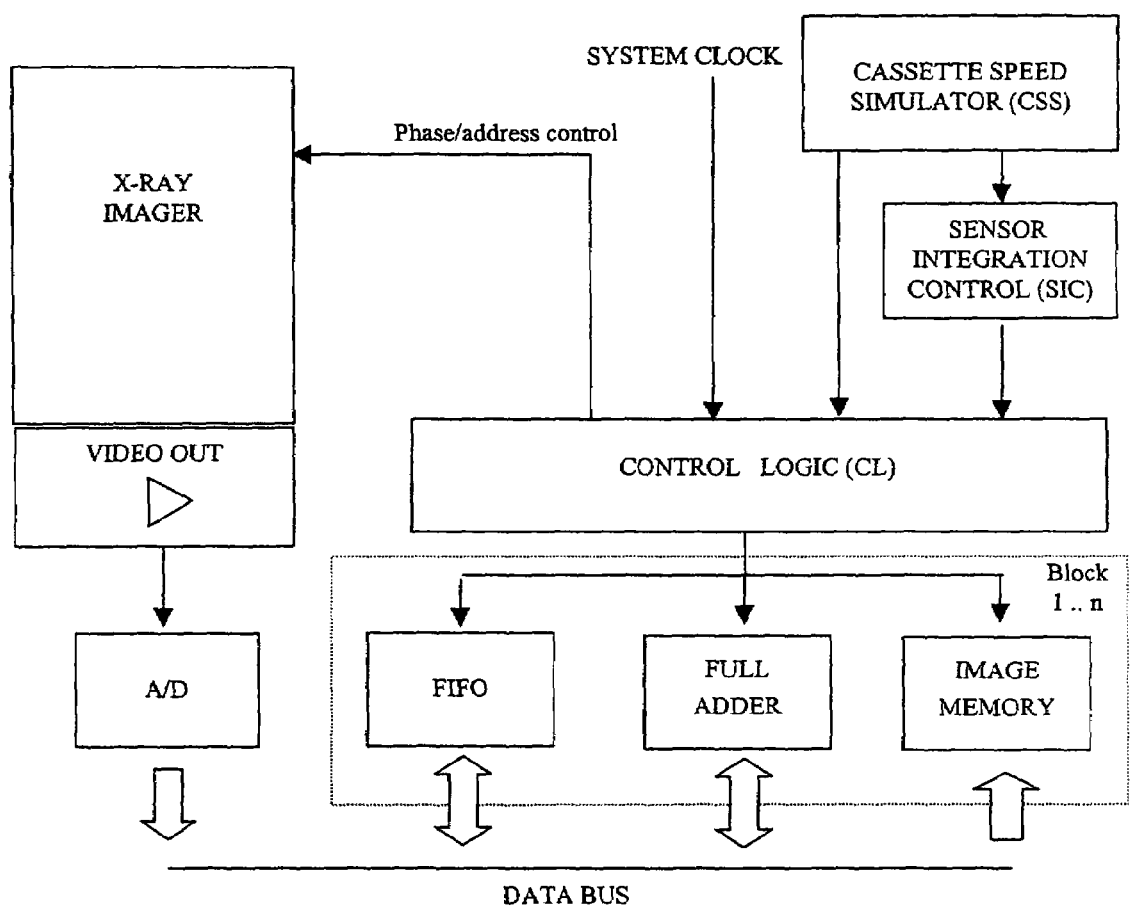
FIG_2: System block diagram

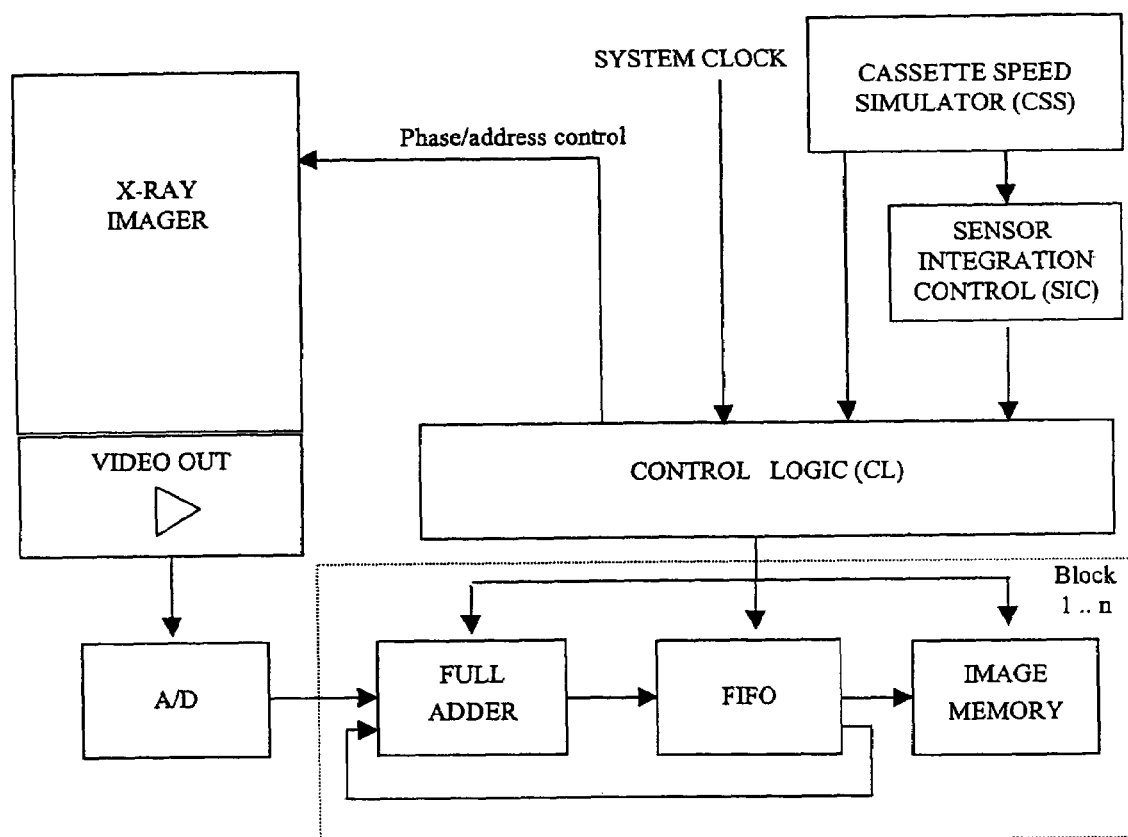
FIG_3: System block diagram ("cascade architecture")

REAL-TIME DIGITAL X-RAY IMAGING APPARATUS

CROSS-REFERENCE TO RELATED APPLICATIONS

This application is a continuation of application Ser. No. 10/205,257 filed Jul. 25, 2002, now U.S. Pat. No. 7,016,461.

BACKGROUND OF THE INVENTION

Orthopantomography, Scannography, Linear Tomography and Cephalography are complementary radiographic techniques, often combined in a single equipment, of widespread use in dental radiology to obtain respectively a comprehensive survey of the maxillo-facial complex, tomographic views of selected anatomical districts under transversal or axial projections, and cranial views under multiple projections, supporting the diagnosis in the dental prevention, restoration and follow up.

Orthopantomography aims to produce a radiographic image of a curved plane approximating the patient jaws, with blurring of the anatomical structures laying outside a narrow layer around the predesignated curved plane, by using the relative movement of the radiographic film versus the rotation of the x-ray source to generate the layer forming effect.

Scannography has a layer forming process similar to Orthopantomography, where the object is typically laying on a flat plane. It is practically used to produce axial or transverse views of specific anatomical districts, such as the jaw, the joints and the sinus.

Linear Tomography is an alternative technique, using the classic linear tomographic layer forming projection. It is practically used to produce axial or transverse views of specific anatomical districts in the jaw.

Cephalography is a stationary radiographic technique, aiming to produce radiographic images of the cranial complex under various projections, with minimum magnification and geometrical distortion.

For all radiographic modalities the real-time digital x-ray image acquisition is nowadays a more and more interesting option, allowing removal of the film processing and related chemicals, by taking advantage of the improved performances and reduced costs provided by the modem image sensor technology.

Prior art (U.S. Pat. No. 4,188,537) describes apparatus and methods in which Realtime Digital Panoramic Radiography is implemented by an array of multiple detectors, or a vertical scanning single detector, where vertical lines are acquired in synchronisation with the rotation movement, so generating and displaying a panoramic image. This solution is deficient, as it is lacking the layer forming effect.

Other prior art (U.S. Pat. No. 4,878,234) describes apparatus and methods in which Real-time Digital Panoramic Radiography is implemented by CCD image sensors where vertical lines in the image zone are clocked out in the not-illuminated storage zone, by a frequency simulating the speed of the moving x-ray film in the conventional Dental Panoramic Tomography.

In other prior art arrangements (U.S. Pat. No. 4,823,369) Real-time Digital Panoramic Radiography is implemented by x-ray image detectors, preferably consisting of amorphous silicon, where complete frames corresponding to the active area are acquired at sufficiently fast frequency and adjacent frames are added as a function of time, either by pre-processing in order to obtain the panoramic image on one selected layer, or by storing in memory and later processing, so giving the possibility of multiple layer reconstruction.

Further prior art arrangement (U.S. Pat. No. 4,995,062) describes apparatus and methods in which Real-time Digital Panoramic Radiography is implemented by CCD image sensors where different vertical lines are driven with different clock frequency so simultaneously obtaining a plurality of tomograms at different depths of the jaw.

Another prior art arrangement (U.S. Pat. No. 5,195,114) describes apparatus and methods in which Real-time Digital Panoramic Radiography is accomplished by an X-ray image detection system, typically based on a signal intensifier tube camera (SIT), where video signal is acquired and stored in a storage unit (such as video tape recorder), and frame digital data are lately derived by A/D conversion and processed selecting frame interval and shift depending on the movement speed of the target, to digitally form the panoramic image of given tomographic layers. This arrangement is limited in the video rate acquisition, and does not provide enough resolution for adequate panoramic image reconstruction. The process is also time consuming and, in case of digital frame storage, would require huge amount of memory.

More recent prior art arrangement (EP 0 673 623) describes apparatus and methods in which Real-time Digital Panoramic Radiography is implemented by X-ray detection system having an area coincident with the cross-section area of the X-ray and so requiring only one narrow slit X-ray diaphragm located on the X-ray source. By this arrangement the Panoramic image reconstruction is accomplished either by frame acquisition, with intermediate frame storage (memory consuming option) or with immediate frame processing (less memory consuming option), or by the TDI method: in the first case for adequate layer formation the frame resolution must be chosen in a way to ensure that each point of the final reconstructed image is represented in more positionally shifted images (preferably five or more); in the second case (even less memory consuming) the image is directly integrated and formed on the X-ray detector, by controlling the clock sequence in a way to ensure that the projected image of a point within the sharp layer of the object will be represented by the same spatial position in the final reconstructed panoramic image.

In Digital Panoramic Radiography, the following desirable features are applicable:

To be able to generate simultaneously a plurality of panoramic tomograms at different depths of the jaw.

To have an accurate, reproducible and inexpensive method of simulating the speed of the x-ray detector (the radiographic film). This information is necessary for the layer forming processing required in the tomosynthesis of the panoramic image.

In the case where full frame acquisition is used, to have a method to adapt to the varying dynamic of the exposure signal in a way to optimise the signal response of the detector in terms of signal to noise ratio.

Both in Real-time Digital Panoramic Radiography, Transversal Tomography and Cephalography it is another desirable feature to have a common electronic hardware capable of serving with efficient and fast response x-ray image sensors of various kind and structure and different scanning methods such as TDI or frame transfer.

The purpose of this invention is to advantageously offer technically efficient and economic solution to all the desirable features above.

SUMMARY OF THE INVENTION

The object of the invention is a x-ray apparatus and methods capable of performing Real-time Digital Radiography with particular application in Orthopantomography, Scannography, Linear Tomography and Cephalography.

In Digital Orthopantomography and Scannography, the apparatus of the invention will implement the following innovating features:

Simultaneous generation of a plurality of panoramic tomograms at different depths of the jaw.

Digital simulation of the speed of the x-ray detector (the radiographic film), by a frequency modulated signal directly synthesized under microprocessor control, providing accurate reproduction of the motor phase signal with phase continuity control and motion direction sensing.

In the case where full frame acquisition is used, automatic adaptation of the frame acquisition frequency to the actual speed of the cassette unit. By this method the dynamic of the exposure signal is reduced, and a better optimization of the signal response of the x-ray detector is achieved.

In Real-time Digital Panoramic Radiography, Transversal Tomography and Cephalography the apparatus will use an innovative common electronic hardware and software solution, capable of serving with efficient and fast response x-ray image sensors of various kind and structure and different scanning methods such as TDI or frame transfer.

The invention is particularly advantageous in dental radiography, where the outlined features find immediate application, but it could also be advantageously employed in other medical and non-medical applications having similar requirements.

Here following is a description in greater detail of the invention, based on the exemplary embodiment illustrated in the attached drawings.

DESCRIPTION OF DRAWINGS AND TABLES

FIG. 1 is a diagram showing an exemplary system dedicated to dental application.

FIG. 2 is a flow chart illustrating the main apparatus functional units.

FIG. 3 is a block diagram illustrating the main apparatus functional units in cascade architecture.

DETAILED DESCRIPTION

The system illustrated in FIG. 1 is a typical dental x-ray diagnostic system performing Real-time Digital Radiography in Orthopantomography, Scannography, Linear Tomography and Cephalography.

For those skilled in the art, it is intended that:

Orthopantomography is a narrow beam scanning technique aiming to reproduce in a single radiographic view the whole or part of a curve plane approximating the patient jaw, using layer forming methods by which the points laying in the target plane are reproduced on the same point of the radiographic image, while points laying outside the target plane are blurred out.

Scannography is a narrow beam scanning technique aiming to reproduce in a single radiographic view the whole or part of a flat plane approximating specific anatomical regions (such as the jaw, the joints, the sinus), using layer forming methods by which the points laying in the target plane are reproduced on the same point of the radiographic image, while points laying outside the target plane are blurred out.

Linear tomography is a wider beam radiographic technique, using the classic linear tomographic layer forming projection, where by the combined movement of x-ray source and x-ray imager around the object, only the points laying in the target plane are reproduced on the same point of the radiographic image, while points laying outside the target plane are blurred out.

Cephalography is a stationary radiographic technique, where the cranial complex is exposed under various projections, with minimum magnification and geometrical distortion.

With reference to FIG. 1:

The x-ray source 1 is aligned with the image receptor 2 (the x-ray imager) by a suitable connecting arm for panoramic radiography and tomography.

The x-ray source 1 can also be tilted and aligned with the image receptor 3 (the x-ray imager) by another connecting arm for performing cephalographic exposure.

Eventually a suitable translation mechanism will allow image receptor 2 to be relocated in position of image receptor 3 for performing cephalography with a unique x-ray imager.

The system is capable of performing orbital projections around the patient skull with simultaneous acquisition, by the x-ray detector, of the imaging data necessary for the reconstruction of the diagnostic image.

Depending on the applicable technique, the system will use a scanning process, with or without layer forming processing, to build up the diagnostic image in panoramic radiography and in transversal or axial tomography.

The Image Processing Unit 4 (IPU) performs the diagnostic image processing and reconstruction. In case of Orthopantomography or Scannography it will use the cassette motor control simulated signal as an input to modulate the frame rate acquisition.

The IPU is made of basic blocks, typically associated to corresponding blocks of the x-ray imager, consisting of: the shared data bus, the A/D converter, the FIFO Registry, the Full Adder, the Control Logic, the Cassette Speed Simulator, The Sensor Integration Control, and the Image Memory.

Here following is a description in greater detail of the functional units composing the apparatus of the invention, which also makes reference to the system block diagram in FIG. 2 and FIG. 3.

The X-ray imager is intended as the x-ray image sensor of any kind, providing either intermediate conversion of x-rays to light (for example by a suitable scintillator layer, with or without fiber optics coupling) or providing direct conversion of x-rays to electric charge (for example by adopting direct x-ray detection layers and bonding technique to the readout layer).

The read out section of the sensor can be a CCD device, controlled by phase control signals generated by the Control Logic, and operated in either of the following two modes:

Full Frame, where the entire image is transported line by line, by charge transfer during irradiation, to the readout registers where the pixel readout is done through the output amplifier.

Frame Transfer, where the entire image is first quickly transported during irradiation to the storage section (obscured from irradiation), and then the entire frame is read out as above.

Or it can be a CMOS device, where the control signals generated by the Control Logic sequence, by column and rows counters, the addressing and read out of the matrix pixels in whatever arrangement is foreseen (by line, by column, by windowing, etc.).

The A/D converter receives as an input the video out signal generated by the x-ray sensor and converts it into digital form, with a resolution, which typically ranges from 8 to 16 bit, synchronized with the pixel rate by the Control Unit. The digital pixel data are readable through the parallel data bus.

The parallel data bus is the data channel through which the pixel data are exchanged between the A/D converter (out only), the FIFO registry (in and out), the Full Adder (in and out) and the Image Memory (in only).

The whole data bus operation is governed by the Control Logic.

The Control Logic contains all the programmable logic to generate the phase sequence and/or addressing for the x-ray sensor and the control signals to govern the enable and data exchange between the FIFO Registry, the Full Adder and the Image Memory through the data bus.

The FIFO Registry represents the temporary storage device, where the pixel data are stored, processed and shifted before transfer to the image memory.

The dimension and organization of the FIFO Registry depends on the operating mode and structure of the x-ray sensor acquisition (by frame, by column, by pixel window, etc.).

The Full Adder is an arithmetic unit performing add operation on the FIFO data.

The Cassette Speed Simulator (CSS), is the functional unit dedicated to the synthesis of the frequency signal simulating the speed of the film cassette.

The input is the digital data referred to the cassette speed for a given projection. Such digital data represent the actual speed over a time interval (a typical interval is 20 msec).

The simulator operates on the base of the system clock frequency (typically 48 MHz) and in response to the input velocity data (with minimum 12 bit resolution) directly synthesizes the output frequency simulating the cassette drive speed, ensuring phase continuity operation by the mechanism of Direct Digital Synthesis (DDS) with phase accumulation, as well known to those skilled in the art.

Additionally the DDS synthesizer can be fashioned in a "Multi Channel" arrangement, in order to provide an economic solution for the simultaneous simulation of multiple speed profiles. For example it may be advantageously used to generate more cassette speed profiles on projections referred to different positions of the layer in focus.

The frequency output signal can be immediately utilized by the Control Logic to govern the shift operation in the TDI mode, directly on the sensor, or in the pseudo-TDI mode during processing on the FIFO Registry.

The Sensor Integration Control is a functional unit receiving as an input the current cassette speed, and providing as an output the corresponding varying duration of the integration time on the sensor. This output is used by the Control Logic to govern the frame acquisition rate and the consequent data processing.

This is particularly useful in case of frame acquisition, where it is not wise to perform frame acquisition always at maximum rate. Especially in phases of the projection where the speed is lower the frame acquisition rate can be reduced, still maintaining adequate frame resolution in view of image reconstruction.

In fact in practical applications the film speed reduction usually accompanies to reduced irradiation, so intrinsically giving a stabilized level of the exposure rate on the sensor.

Therefore the adjustment of the sensor integration time in dependence of the cassette speed leads to a reduced dimensioning of the x-ray exposure dynamic of the image sensor, so favoring in general an improved signal to noise response of the same sensor. In a typical application the Sensor Integration Time (SIT) may relate with the Actual Cassette Speed (ACS) as follows: SIT (s)=$\frac{1}{10}$*ACS (mm/s)

The Image Memory is the storage device where the image data are deposited after processing. Typically the image data are stored column by column in adjacent positions, up to form the complete image.

Eventually more image memories can be used at the same time, corresponding to images generated from projections referred to different positions of the layer in focus.

As a particular application of the general arrangement described above, the more general parallel data bus structure can conveniently be implemented using the simplified structure of FIG. 3, where the Full Adder and the FIFO are arranged in "cascade architecture".

The "cascade architecture" may either be embedded in the hardware, such as in the case of using FPGA type Programmable Logic Devices, or implemented in the software micro code, such as in the case of using Digital Signal Processor devices.

Based on the functional units above, the methods of this invention will be based on various operating steps of the IPU, depending on the radiographic modality chosen, the sensor type and the foreseen acquisition mode.

In Orthopantomography and Scannography the following cases apply:

(a) Case of a CCD sensor Full Frame, with direct integration and TDI operation on-the-sensor.

The signal is directly integrated on the sensor, while the speed simulated signal is used to govern the column shift operation on the sensor.

The last column is shifted in the readout register and it is readout pixel by pixel through the A/D converter into the FIFO Registry.

On termination the entire column is transferred from the FIFO Registry to the Image Memory, adjacent to the previously acquired column.

(b) Case of CCD Sensor Driven in Frame Transfer, with Pseudo-TDI image reconstruction.

At regular intervals, as dictated by the Control Logic under input from the SIC, the entire image is integrated and then quickly transported during irradiation to the storage section (obscured from irradiation).

Then pixel by pixel the entire frame is read out into the FIFO Registry. Depending on the sequence dictated by the Control Logic in response to the CSS, the individual pixel is added to the corresponding pixel in the FIFO Registry.

On termination the columns of the FIFO Registry are shifted, and the last column is moved into the Image Memory, adjacent to the previously acquired column.

(c) Case of CMOS sensor, with pseudo-TDI image reconstruction.

At regular intervals, as dictated by the Control Logic under input from the SIC, the entire image is scanned with sequential pixel addressing and read out, by rows or by columns, eventually applying a useful window within the sensor active area.

Depending on the sequence dictated by the Control Logic in response to the CSS, the individual pixel is added to the corresponding pixel in the FIFO Registry.

On termination all the columns of the FIFO Registry are shifted, and the last column of the Registry is moved into the Image Memory, adjacent to the previously acquired column.

In Linear Tomography the CSS and SIC are not active. The following cases apply:

(a) Case of a CCD sensor Full Frame, with direct integration on-the-sensor.

The signal is directly integrated on the sensor during the whole time of irradiation. On termination the image is shifted column by column to the readout register and is readout pixel by pixel through the A/D converter into the FIFO Registry.

On termination the entire column is transferred from the FIFO Registry to the Image Memory, adjacent to the previously acquired column.

(b) Case of CCD sensor driven in Frame Transfer.

At regular intervals, as dictated by the frame acquisition rate from the Control Logic, the entire image is integrated and then quickly transported during irradiation to the storage section (obscured from irradiation).

Then pixel by pixel the entire frame is added to the corresponding pixel in the FIFO Registry, so building up the image by digital integration.

On termination the entire image is moved, by column shifting, from the FIFO Registry into the Image Memory.

(c) Case of CMOS Sensor, with direct integration on-the-sensor.

The signal is directly integrated on the sensor during the whole time of irradiation. On termination the sensor is scanned pixel by pixel (eventually within a specified window) and the image data are directly transferred to the Image Memory.

(d) Case of CMOS sensor driven in Frame Transfer.

At regular intervals, as dictated by the Control Logic, the entire image is scanned with sequential pixel addressing and read out, by rows or by columns, eventually applying a useful window within the sensor active area.

Then pixel by pixel the entire frame is added to the corresponding pixel in the FIFO Registry, so building up the image by digital integration.

On termination the entire image is moved, by column shifting, from the FIFO Registry into the Image Memory.

In Cephalography, a scanning method is applied, where the rigid coupling of x-ray source and sensor is translated either horizontally or vertically across the object, and the sensor is exposed with a narrow collimated x-ray beam.

The CSS and SIC are not active. The following cases apply:

(a) Case of a CCD sensor Full Frame, with direct integration on-the-sensor.

The signal is directly integrated on the sensor. The irradiation is continuous, while the sensor columns are shifted by the Control Logic at a speed such to ensure the coincidence on the same column of the projection of the same object point laying in the mid sagittal plane of the patient head.

The last column is shifted to the readout register and is readout pixel by pixel through the A/D converter into the FIFO Registry.

On termination the entire column is transferred from the FIFO Registry to the Image Memory, adjacent to the previously acquired column.

(b) Case of CCD sensor driven in Frame Transfer.

At regular intervals, as dictated by the frame acquisition rate from the Control Logic, the entire image is integrated and then quickly transported during irradiation to the storage section (obscured from irradiation).

Then pixel by pixel the entire frame is added to the corresponding pixel in the FIFO Registry, so building up the image by digital integration.

The frame in the FIFO Registry is also shifted by the Control Logic at a speed such to ensure the coincidence on the same column of the projection of the same object point laying in the mid sagittal plane of the patient head.

The last shifted column of the FIFO Registry is moved into the Image Memory, adjacent to the previously acquired column.

As alternative method, applicable in case of higher intensity pulsed exposure sequence, the entire image is integrated during one exposure flash and then, after the exposure, it is quickly transported to the storage section.

The entire frame is then readout and transferred in the FIFO Registry, so building up one vertical strip of the image.

The whole or part of the frame in the FIFO Registry is therefore moved, by column shifting, into the Image Memory, adjacent to the previously acquired strip.

The above sequence is repeated with the next exposure flash taking place in the next adjacent position of x-ray source and sensor.

(c) Case of CMOS sensor driven in Frame Transfer.

At regular intervals, as dictated by the frame acquisition rate from the Control Logic, the entire image is integrated and then quickly readout pixel by pixel through the A/D converter.

The readout frame is added to the corresponding pixel in the FIFO Registry, so building up the image by digital integration.

The frame in the FIFO Registry is also shifted by the Control Logic at a speed such to ensure the coincidence on the same column of the projection of the same object point laying in the mid sagittal plane of the patient head.

The last shifted column of the FIFO Registry is moved into the Image Memory, adjacent to the previously acquired column.

As alternative method, applicable in case of higher intensity pulsed exposure sequence, the entire image is integrated during one exposure flash and then, after the exposure, it is quickly readout and transferred in the FIFO Registry, so building up one vertical strip of the image.

The whole or part of the frame in the FIFO Registry is therefore moved, by column shifting, into the Image Memory, adjacent to the previously acquired strip.

The above sequence is repeated with the next exposure flash taking place in the next adjacent position of x-ray source and sensor.

It is an advantage of the present invention that by simple replicating the above FIFO Registry, the CSS, the SIC and the destination Image Memory, image reconstruction on more layers in Orthopantomography and Scannography can be easily achieved.

It would be in fact very useful, for example, that the clinician can pre select by the user interface more layers around the principal layer in focus and the apparatus can instantly process and generate on the equipment the corresponding diagnostic images ready for transfer to a host computer, without need of huge amount of memory for storage of all the acquired frames, or huge data transfer rates for transfer of the whole series of frames to the host computer.

It is prerequisite that the electronic structure above provides sufficient processing speed to accomplish with the required computation load.

For example considering a cassette speed range up to 30 mm/s, as typically used in Orthopantomography, and a pixel size of 0,1 mm, frame acquisition rates up to 600 f/s shall be possible.

In case of multiple layer reconstruction, the electronics shall be fast enough to process each acquired frame for each of the various layers foreseen.

In case of a 30,000 pixels sensor block with 3 layers reconstruction an overall frequency of 54 MHz is required.

It is another advantage of the present invention the possibility to easily accomplishing with projections having reverse rotation movement, provided that the used sensor allows for right and left readout of the pixel matrix.

This is particularly useful in the case where symmetric projections are achieved by simple replicating the same projection digital structure with reversed rotation, so allowing reduction of the memory space necessary for projection data storage.

The present invention provides a dental x-ray diagnostic apparatus performing Real-time Digital Radiography in various modalities such as Orthopantomography, Linear Tomography, Scannography and Cephalography. It includes (referring to FIG. 1):

A. An x-ray source 1, rigidly connected with an x-ray imager 2, providing x-ray generation, equipped with collimating means to provide limitation of the radiation incident on the x-ray imager.

B. An x-ray imager 2, preferably rigidly connected and aligned with the x-ray source 1, and being electrically coupled to a suitable Image Processing Unit 3.

C. A cinematic unit 4, allowing execution of orbital movements of x-ray source 1 and x-ray imager 2 around the patient skull, allowing projections as required for Orthopantomography, Scannography and Tomography.

D. A mechanism to allow alignment of the x-ray source with another x-ray imager 5, for performing Cephalography, or alternatively allowing relocation of the same x-ray imager in the position 5 for Cephalography.

E. An Image Processing Unit (IPU) 3, performing the x-ray imager control and the image processing functions, composed by the following functional units (refer to FIG. 2 and FIG. 3):

(a) The Control Logic

Functional unit containing all the programmable logic to generate the phase sequence and/or addressing for the x-ray imager and the control signals to govern the enable and data exchange between the FIFO Registry, the Full Adder and the Image Memory through the data bus.

(b) The A/D Converter

Functional unit performing the analogue to digital conversion of the video out signal generated by the x-ray imager, synchronized with the pixel rate by the Control Logic. The digital pixel data output is readable through the parallel data bus.

(c) The Parallel Data Bus

The data channel through which the pixel data are exchanged between the A/D converter (out only), the FIFO registry (in and out), the Full Adder (in and out) and the Image Memory (in only).

The whole data bus operation is governed by the Control Logic.

(d) The FIFO Registry

Functional unit representing the temporary storage device, where the pixel data are stored, processed and shifted before transfer to the image memory.

The dimension and organization of the FIFO Registry depends on the operating mode and structure of the x-ray sensor acquisition (by frame, by column, by pixel window, or the like).

(e) The Full Adder.

Functional unit performing add operation on the FIFO data.

(f) The Cassette Speed Simulator (CSS).

Functional unit dedicated to the synthesis of the frequency signal simulating the speed of the film cassette.

The input is the digital data referred to the cassette speed for a given projection. Such digital data represent the actual speed over a time interval (a typical interval is 20 msec).

The simulator operates on the base of the system clock frequency (typically 48 MHz) and in response to the input velocity data (with minimum 12 bit resolution) directly synthesizes the output frequency simulating the cassette drive speed, ensuring phase continuity operation by the mechanism of Direct Digital Synthesis (DDS) with phase accumulation, conventional and known to those skilled in the art. The frequency output signal can be substantially immediately utilized by the Control Logic to govern the shift operation in the TDI mode, directly on the sensor, or in the pseudo-TDI mode during processing on the FIFO Registry.

(g) The Sensor Integration Control (SIC)

Functional unit receiving as an input the current cassette speed, and providing as an output the corresponding varying duration of the integration time on the sensor. This output is used by the Control Logic to govern the frame acquisition rate and the consequent data processing.

This is particularly useful in case of frame acquisition, where it is not wise to perform frame acquisition always at maximum rate. Especially in phases of the projection where the speed is lower the frame acquisition rate can be reduced, still maintaining adequate frame resolution in view of image reconstruction.

In practical applications the film speed reduction usually accompanies reduced irradiation, thereby intrinsically providing a stabilized level of the exposure rate on the sensor. Therefore the adjustment of the sensor integration time in dependence of the cassette speed leads to a reduced dimensioning of the x-ray exposure dynamic of the image sensor, so favoring in general an improved signal to noise response of the same sensor. In a typical application the Sensor Integration Time (SIT) may relate with the Actual Cassette Speed (ACS) as follows: SIT (s)=$\frac{1}{10}$*ACS (mm/s)

(h) The Image Memory

It is the storage unit where the image data are deposited after processing. Typically the image data are stored column by column in adjacent positions, up to form the complete image.

Eventually more image memories can be used at the same time, corresponding to images generated from projections referred to different positions of the layer in focus.

The X-ray imager 2 is an x-ray image sensor of any conventional design, providing either intermediate conversion of x-rays to light (for example by a suitable scintillator layer, with or without fiber optics coupling) or providing direct conversion of x-rays to electric charge (for example by adopting a direct x-ray detection layer and bonding technique to the readout layer).

The X-ray imager 2 may have a read out section made of a CCD device, controlled by phase control signals generated by the Control Logic, and operated in Full Frame mode, where the entire image is transported line by line, by charge transfer during irradiation, to the readout registers, where the pixel readout is done through the output amplifier.

The X-ray imager 2 may also be an x-ray image sensor having the read out section made of a CCD device, controlled by phase control signals generated by the Control Logic, and operated in Frame Transfer mode, where the entire image is first quickly transported during irradiation to the storage section (obscured from irradiation), and then the entire frame is transported line by line, by charge transfer, to the readout registers, where the pixel readout is done through the output amplifier. It may also be an x-ray image sensor having the read out section made of a CMOS device, where the control signals are generated by the Control Logic sequence, by column and rows counters, the addressing and read out of the matrix pixels under any of several conventional arrangements, including for example, by line, by column, by windowing, and the like.

The IPU functional structure is preferably replicated, two or more times, allowing in Orthopantomography and Scannography simultaneous image reconstruction on more layers. It is preferably accompanied with the control given to the user to preselect by a suitable user interface, analog or digital, multiple layers around the principal layer in focus.

It is also possible according to the present invention, to perform image reconstruction in Orthopantomography and Scannography both with clockwise and counterclockwise orbital movements, either by using CCD sensors with dual readout register structure, or by using FIFO Registry with bi-directional shift operation.

According to one embodiment of the invention, a "Multi Channel" configuration of the CSS functional unit is advantageously used, where multiple profiles are simulated at the same time, corresponding for example to cassette speeds on projections referred to different positions of the layer in focus.

As a particular application of the more general parallel data structure, the Full Adder and the FIFO according to the invention, may be organized in a "cascade architecture" either embedded in the hardware, such as in the case of using FPGA type Programmable Logic devices, or implemented in the software micro code, such as in the case of using Digital Signal Processor devices.

A method for operating a dental x-ray diagnostic apparatus performing Realtime Digital Radiography in Orthopantomography and Scannography, comprises the steps of:
  Irradiating the patient skull during the orbital movement of x-ray source and x-ray imager.
  Controlling by the 055 signal the column shift operation on the x-ray imager.
  Shifting the last column in the readout register, and reading it out pixel by pixel through the A/D converter into the FIFO Registry.
  On termination transferring the entire column from the FIFO Registry to the Image Memory, adjacent to the previously acquired column, so building up the whole diagnostic image.

This inventive method is particularly applicable to x-ray imagers having a readout section made of a CCD sensor operated in Full Frame, with direct integration and TDI operation on-the-sensor.

A method for operating a dental x-ray diagnostic apparatus performing Real-time Digital Radiography in Orthopantomography and Scannography, comprises the steps of:
  Irradiating the patient skull during the orbital movement of x-ray source and x-ray imager.
  Controlling at regular intervals, as dictated by the Control Logic under input from the SIC, the frame integration and the quick frame transfer during irradiation to the storage section (obscured from irradiation).
  Reading the entire frame out from the storage section through the A/D converter, and adding it, pixel by pixel, to the FIFO Registry.
  Shifting the frame columns in the FIFO Registry, based on the sequence dictated by the Control Logic in response to the CSS.
  Transferring the last shifted column from the FIFO Registry to the Image Memory, adjacent to the previously acquired column, so building up the whole diagnostic image.

This method is particularly applicable to x-ray imagers having a readout section made of a CCD sensor operated in Frame Transfer mode, with pseudo-TDI image reconstruction.

A method for operating a dental x-ray diagnostic apparatus performing Real-time Digital Radiography in Orthopantomography and Scannography, comprises the steps of:
  irradiating the patient skull during the orbital movement of x-ray source and x-ray imager.
  Controlling at regular intervals, as dictated by the Control Logic under input from the SIC, the frame integration and quick readout during irradiation through the A/D converter, and the frame adding, pixel by pixel, to the FIFO Registry.
  Shifting the frame columns in the FIFO Registry, based on the sequence dictated by the Control Logic in response to the OSS.
  Transferring the last shifted column from the FIFO Registry to the Image Memory, adjacent to the previously acquired column, so building up the whole diagnostic image.

This method is particularly applicable to x-ray imagers having a readout section made of a CMOS sensor operated in Frame Transfer mode, with pseudo-TDI image reconstruction.

A method for operating a dental x-ray diagnostic apparatus performing Real-time Digital Radiography in Linear Tomography, comprising the steps of:
  Irradiating the patient skull during the orbital movement of x-ray source and x-ray imager.
  On termination of irradiation, shifting the whole frame, column by column, to the readout register.
  Reading out, for each shifted column, the readout register through the A/D converter, and moving it, pixel by pixel, to the FIFO Registry.
  Moving the last readout column from the FIFO Registry to the Image Memory, adjacent to the previously acquired column, so building up the whole diagnostic image.

This method is particularly applicable to x-ray imagers having a readout section made of a CCD sensor operated in Full Frame mode.

A method for operating a dental x-ray diagnostic apparatus performing Real-time Digital Radiography in Linear Tomography, comprises the steps of:
  Irradiating the patient skull during the orbital movement of x-ray source and x-ray imager.
  On termination of irradiation, reading out the whole frame through the A/D converter, and moving it, pixel by pixel, to the FIFO Registry.
  Moving the whole frame, by column shifting, from the FIFO Registry to the Image Memory.

This method is particularly applicable to x-ray imagers having a readout section made of a CMOS sensor with full integration on-the-sensor.

A method for operating a dental x-ray diagnostic apparatus performing Real-time Digital Radiography in Linear Tomography, comprising the steps of:
  Irradiating the patient skull during the orbital movement of x-ray source and x-ray imager.

Controlling at regular intervals, as dictated by the Control Logic, the frame integration and the quick frame transfer during irradiation to the storage section (obscured from irradiation).

Reading the entire frame out from the storage section through the A/D converter, and adding it, pixel by pixel, to the FIFO Registry.

On termination of irradiation, moving the whole frame from the FIFO Registry to the Image Memory.

This method is particularly applicable to x-ray imagers having a readout section made of a CCD sensor operated in Frame Transfer mode.

A method for operating a dental x-ray diagnostic apparatus performing Real-time Digital Radiography in Linear Tomography, comprising the steps of:

Irradiating the patient skull during the orbital movement of x-ray source and x-ray imager.

Controlling at regular intervals, as dictated by the Control Logic, the frame integration and the frame readout, pixel by pixel, through the A/D converter. Eventually, a useful window may be applied within the sensor active area.

Adding the readout data, pixel by pixel, to the FIFO Registry, so building up the image by digital integration.

On termination of irradiation, moving the whole frame from the FIFO Registry to the Image Memory.

This method is particularly applicable to x-ray imagers having a readout section made of a CMOS sensor driven in Frame Transfer mode.

A method for operating a dental x-ray diagnostic apparatus performing Real-time Digital Radiography in Cephalography, comprises the steps of:

Irradiating the patient skull under cephalographic projection, while x-ray source and x-ray imager perform a linear scanning movement.

Shifting the sensor columns, as dictated shifted by the Control Logic, at a speed such to ensure the coincidence on the same sensor column of the projection of the same object point laying in the mid sagittal plane of the patient head.

Shifting of the last column in the readout register, and reading out pixel by pixel through the A/D converter into the FIFO Registry.

Moving the last readout column from the FIFO Registry to the Image Memory, adjacent to the previously acquired column, so building up the whole diagnostic image.

This method is particularly applicable to x-ray imagers having a readout section made of a CCD sensor operated in Full Frame mode.

A method for operating a dental x-ray diagnostic apparatus performing Real-time Digital Radiography in Cephalography, comprises the steps of:

Irradiating the patient skull under cephalographic projection, while x-ray source and x-ray imager perform a linear scanning movement.

At regular intervals, as dictated by the frame acquisition rate from the Control Logic, integrating and quickly moving the frame during irradiation to the storage section (obscured from irradiation).

Reading the entire frame out from the storage section through the A/D converter, and adding it, pixel by pixel, to the FIFO Registry.

Shifting the frame columns in the FIFO Registry, as dictated by the Control Logic, at a speed such to ensure the coincidence on the same column of the projection of the same object point laying in the mid sagittal plane of the patient head.

Moving the last shifted column from the FIFO Registry to the Image Memory, adjacent to the previously acquired column, so building up the whole diagnostic image.

This method is particularly applicable to x-ray imagers having a readout section made of a CCD sensor operated in Frame Transfer mode.

A method for operating a dental x-ray diagnostic apparatus performing Real-time Digital Radiography in Cephalography, comprising the steps of:

Irradiating the patient skull under cephalographic projection, while x-ray source and x-ray imager perform a linear scanning movement, where x-ray pulses are synchronized with the scanning movement.

At intervals synchronized with the x-ray pulses by the Control Logic, integrating and quickly moving the frame after irradiation to the storage section (obscured from irradiation).

Reading the entire frame out from the storage section through the A/D converter, and adding it, pixel by pixel, to the FIFO Registry, so building up one vertical strip of the image.

Moving the whole or part of the frame in the FIFO Registry to the Image Memory, adjacent to the previously acquired strip, so building up the whole diagnostic image.

Repeating the above sequence with the next exposure flash, taking place in the next adjacent position of x-ray source and sensor.

This method is particularly applicable to x-ray imagers having a readout section made of a CCD sensor operated in Frame Transfer mode, used in combination with pulsed irradiation.

A method for operating a dental x-ray diagnostic apparatus performing Real-time Digital Radiography in Cephalography, comprising the steps of:

Irradiating the patient skull under cephalographic projection, while x-ray source and x-ray imager perform a linear scanning movement.

At regular intervals, as dictated by the frame acquisition rate from the Control Logic, integrating and quickly reading out the whole frame during irradiation through the A/D converter, and adding it, pixel by pixel, to the FIFO Registry, so building up the image by digital integration.

Shifting the frame columns in the FIFO Registry, as dictated by the Control Logic, at a speed such to ensure the coincidence on the same column of the projection of the same object point laying in the mid sagittal plane of the patient head.

Moving the last shifted column from the FIFO Registry to the Image Memory, adjacent to the previously acquired column, so building up the whole diagnostic image.

This method is particularly applicable to x-ray imagers having a readout section made of a CMOS sensor operated in Frame Transfer mode.

A method for operating a dental x-ray diagnostic apparatus performing Real-time Digital Radiography in Cephalography, comprises the steps of:

Irradiating the patient skull under cephalographic projection, while x-ray source and x-ray imager perform a linear scanning movement, where x-ray pulses are synchronized with the scanning movement.

At intervals synchronized with the x-ray pulses by the Control Logic, integrating and, after the irradiation, quickly reading out the entire frame, pixel by pixel, through the A/D converter into the FIFO Registry, so building up one vertical strip of the image.

Moving the whole or part of the frame in the FIFO Registry to the Image Memory, adjacent to the previously acquired strip, so building up the whole diagnostic image.

Repeating the above sequence with the next exposure flash, taking place in the next adjacent position of x-ray source and sensor.

This method is particularly applicable to x-ray imagers having a readout section made of a CMOS sensor operated in Frame Transfer mode, used in combination with pulsed irradiation.

By using any of these inventive methods, a user can preselect by the appropriate user interface more or multiple layers of interest around the principal layer in focus and, having replicated the IPU functional structure, in Orthopantomography and Scannography simultaneous image reconstruction on more layers is accomplished.

By using any of these inventive methods, via adequate adjustment by the Control Logic of the direction of the shift operation, either on CCD sensors with dual readout register structure, or on the FIFO Registry, the possibility is given to perform image reconstruction in Orthopantomography and Scannography both with clockwise and counterclockwise orbital movements.

We claim:

1. A dental x-ray apparatus for performing real-time digital radiography of a patient skull, the dental x-ray apparatus comprising:
   an x-ray source to provide x-ray generation;
   an x-ray imager connected to the x-ray source;
   a cinematic unit configured to provide orbital movements of the x-ray source and the x-ray imager around the patient skull for Orthopantomography, Scannography and Tomography;
   an alignment mechanism to align the x-ray source with one of a relocated x-ray imager or a second x-ray imager for Cephalography;
   an image processing unit being electrically coupled to the x-ray imager, the image processing unit comprising:
     a FIFO registry, wherein the FIFO registry comprises a temporary storage device;
     a full adder, wherein the full adder performs an add operation on FIFO data;
     an image memory;
     a data bus to connect the FIFO registry, the full adder and the image memory;
     a Cassette Speed Simulator (CSS); and
     a control logic functional unit, the control logic functional unit comprising programmable logic to generate a phase sequence or addressing function for the x-ray imager and control signals to control enabling and data exchange between the FIFO registry, the full adder and the image memory through the data bus.

2. The dental x-ray apparatus of claim 1, further comprising a functional converter for performing analogue to digital conversion of a video out signal generated by said x-ray imager, synchronized with a pixel rate by said control logic.

3. The dental x-ray apparatus of claim 2, wherein said data bus is a parallel data bus and digital pixel data output from said functional converter is provided to said parallel data bus.

4. The dental x-ray apparatus of claim 3, wherein said parallel data bus is a data channel through which pixel data is exchanged between said converter, said FIFO registry, said Full Adder and said Image Memory.

5. The dental x-ray apparatus of claim 4, wherein pixel data are stored, processed and shifted before transfer to said image memory.

6. The dental x-ray apparatus of claim 1, wherein the CSS provides a synthesis of a frequency signal simulating a speed of a film cassette.

7. The dental x-ray apparatus of claim 6, wherein an input to said CSS is digital data corresponding to the cassette speed for a given projection, thereby representing an actual speed over a time interval.

8. The dental x-ray apparatus of claim 1, wherein the CSS operates on a base of a system clock frequency and in response to input velocity data, synthesizes the output frequency simulating the cassette drive speed, ensuring phase continuity operation by Direct Digital Synthesis with phase accumulation.

9. The dental x-ray apparatus of claim 1, further comprising:
   a sensor integration control configured to receive as an input the cassette speed, and provide as an output a corresponding varying duration of an integration time on the sensor; and
   wherein the output of the sensor integration control is used by the control logic to control a frame acquisition rate.

10. The dental x-ray apparatus of claim 9, wherein an adjustment of the integration time in response to a reduction of the cassette speed results in a reduced dimensioning of an x-ray exposure dynamic of the sensor.

11. The dental x-ray apparatus of claim 1, wherein the FIFO registry and the full adder are organized in a cascade architecture.

12. The dental x-ray apparatus of claim 1, wherein:
   the x-ray imager comprises one of a CCD sensor or a CMOS sensor; and
   the image processing unit is configured to digitally process imaging data from each of an x-ray imager having a CCD sensor and an x-ray imager having a CMOS sensor.

* * * * *